United States Patent [19]

Nisii

[11] 4,327,060
[45] Apr. 27, 1982

[54] STERILIZING-CONTAINING DEVICE FOR DENTAL TOOLS

[76] Inventor: Alessandro Nisii, Via Vallombrosa 18, Rome, Italy

[21] Appl. No.: 145,966

[22] Filed: May 2, 1980

[30] Foreign Application Priority Data

May 8, 1979 [IT] Italy .................... 48978 A/79

[51] Int. Cl.³ .................... A61L 2/06; A61L 2/18
[52] U.S. Cl. .................... 422/300; 206/210; 206/213.1; 206/223; 206/369; 422/301; 422/310
[58] Field of Search ............ 422/297, 299, 301, 300, 422/310; 206/210, 213.1, 368, 369, 223

[56] References Cited

U.S. PATENT DOCUMENTS

| | | | |
|---|---|---|---|
| 1,045,607 | 11/1912 | Payne | 206/210 |
| 1,187,364 | 6/1916 | Monnot | 206/210 |
| 1,576,535 | 3/1926 | Muir | 422/300 X |
| 2,012,380 | 8/1935 | Durham | 206/210 |
| 2,366,369 | 1/1945 | Tannehberg | 422/300 X |
| 2,556,495 | 6/1951 | Freedman | 422/301 |
| 2,786,245 | 3/1957 | Steinbock | 422/301 X |
| 4,050,894 | 9/1977 | Genis | 206/368 X |

Primary Examiner—Barry Richman
Attorney, Agent, or Firm—Bacon & Thomas

[57] ABSTRACT

An open-top container receives a dental tool support in the form of an open-bottom cylinder provided with threads around its upper and lower ends engageable with internal threads at the upper end of the container so that the support may be held by the container in either an upper or lower position. A cap threadedly engages the tool support to seal the assembly when the support is in its lower position.

12 Claims, 4 Drawing Figures

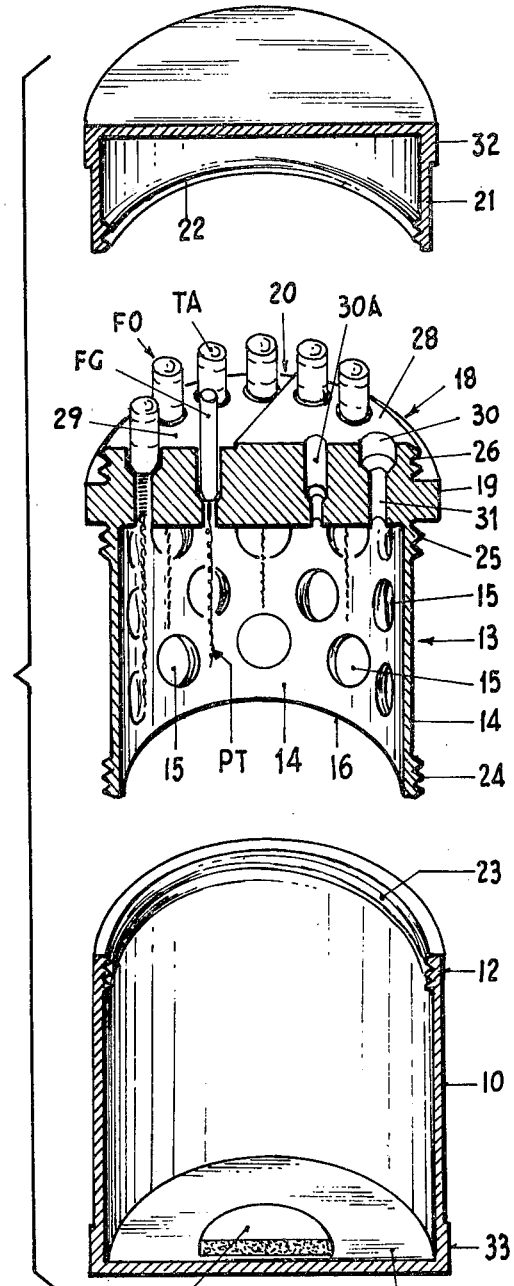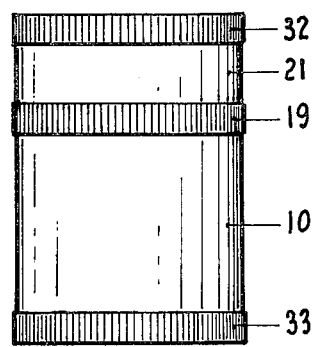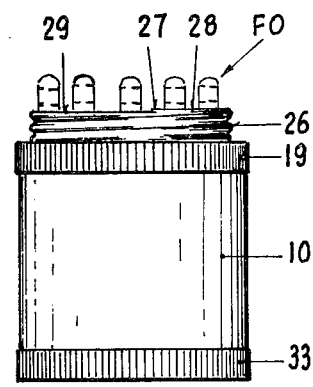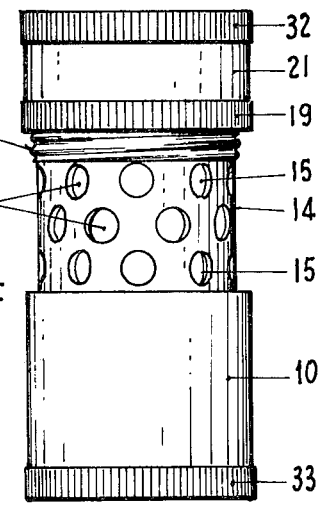

STERILIZING-CONTAINING DEVICE FOR DENTAL TOOLS

BACKGROUND OF THE INVENTION

The invention refers to a sterilizing-containing device for dental tools and, more particularly, tools intended for endodental treatments.

The dentist performs such treatments by means of a number of burrs having different diameters, which burrs can either be manually operated, and accordingly they are provided with a suitable head, or intended to be operated by a dental engine head, thus being provided with a stem adapted to be tightened and gripped into the suitable spindle of the engine head.

These tools, like all dental tools, are to be sterilized and at present they are mainly sterilized by heat processes, both dry and steam processes (within autoclave). However, the tools can be sterilized also chemically either by dipping or by creating a bactericide atmosphere all around the tools, for example by sublimating phthalin tablets.

At present both of these sterilization processes are performed by handling dental burrs like other dental tools, i.e. placing them into a small tray adapted to be introduced into a closed space such as an autoclave, an oven or a sealed chamber, where the sterilization process takes place.

The above results in two types of drawbacks. In the first place it is impossible to personalize the tools, while a personalization should be required owing to the nature of endodental treatments. In the second place the burrs are laid down randomly on the trays and even mixed up with other tools, so that they are to be separated again from each other according to their diameters after each sterilization process.

This is undoubtedly irrational and anachronistic in respect of the technical development occurred in other dental fields.

SUMMARY OF THE INVENTION

Accordingly, it is an object of the invention to overcome the above drawbacks providing a sterilizing container for tools intended for endodental treatments adapted to be used both for performing a technical sterilization, and to this purpose the container is adapted to be introduced into an oven or an autoclave, and for performing a chemical sterilization, thus having such a structure as to receive the sterilizing fluid or tablet thereinto and to be sealed in order to be fluid and gas tight.

It is another object of the invention to provide a sterilizing container wherein these tools are kept in order and separate from each other.

The device according to the invention comprises a container body provided with a sealing cap and having an inner support movable therein from a lowered position wherein the tools are simply held and chemically sterilized to a raised position wherein the tools are exposed and thermally sterilized.

BRIEF DESCRIPTION OF THE DRAWINGS

The invention will be now described in detail with reference to the annexed drawing, wherein:

FIG. 1 is an exploded and axially sectional view of the sterilizing-containing device of the invention;

FIG. 2 is a side elevational view of the device of FIG. 1 in the closed condition for chemical sterilization;

FIG. 3 is a similar elevational view showing the device in the condition of FIG. 2, the cap being removed; and, FIG. 4 is a similar elevational view of the device in the open condition for use and thermal sterilization.

DESCRIPTION OF THE PREFERRED EMBODIMENT

The sterilizing container of the invention substantially comprises: a cylindrical containing body 10 closed at its end 11 and opened at its upper end 12; a cylindrical inner support 13 comprising a cylindrical wall 14 having a plurality of openings 15 arranged in offset positions within three spaced annular sections, which inner support 13 is opened at its lower end 16 and is provided with a head 18 comprising a knurled embossment 19 and an upper closed end 20; and, a screw cap 21 having an inner thread 22.

Cylindrical body 10 has a slightly larger diameter than inner support 13, so as to loosely receive support 13, and has a thread 23 at mouth 12 thereof.

Inner support 13 has a first thread 24 matching thread 23, at the bottom of drilled wall 14, and a second thread 25 also matching thread 23 and placed immediately below knurled embossment 19.

Furthermore, head 18 has a third thread 26 matching thread 22 of cap 21.

Upper wall 20 of head 18 comprises a diametral step 27 defining two semicircles 28 and 29, one semicircle being slightly raised from the other.

Furthermore, upper wall 20 has also a number of cylindrical countersunk cavities or bores 30 each comprising an upper length of larger diameter opening to the outer face of wall 20 and a lower length 31 of smaller diameter opening to the inner face thereof.

Finally, cap 21 comprises an upper knurled rim 32 and an identical knurled rim referred to by 33 is formed at the bottom of cylindrical body 10.

In a sterilizing-containing device having such a construction the burrs for endodental treatments generally referred to by FO and each comprising a cutting portion PT and an operating head TA, are introduced into the openings of upper wall 20 (FIG. 1), head TA being received within upper length 30 and cutting portion PT being fitted into length 31 and protruding therefrom within support 13.

The two halves 28 and 29 of wall 20, besides bores 30 for the headed burrs, also comprise cavities or bores 30A of smaller diameter for stemmed burrs FG.

It should be noted that halves 28 and 29 of upper wall 20 are mirror images of each other and comprise an equal number of bores 30 and 30A. In a preferred embodiment there are six bores 30 and two bores 30A for each half, since a set comprising six burrs is sufficient for endodental treatments.

Evidently, such an arrangement allows each pair of burr sets to be personalized destining the corresponding sterilizing container to a given patient.

In operation, for performing the heat sterilization process, the sterilizing container having the burrs in place will be placed in the condition of FIG. 4 (with or without the cap) within the autoclave or oven, while for performing the chemical sterilization process a tablet of a bactericide substance PD (FIG. 1) or a bactericide fluid (not shown) is introduced into body 10 having the burrs in place, then sealing container 10 by means of cap 21 and leaving it in the closed condition for the time required.

After sterilization the container is kept in the condition of FIG. 3 or 4 at hand of the dentist who can thus readily take the different burrs required for the treatment.

From the foregoing it will be evident that the sterilizing-containing device of the invention completely overcomes the problem of keeping a set of burrs for endodental treatments in order even during the heat sterilization process, also having the further advantage of allowing the chemical sterilization to be autonomously and independently performed.

As far as the chemical sterilization process by means of fluids or vapors is concerned, it should be noted here that matching threads 23 and 25 and 22 and 26, that cooperate when the device is in the condition of FIG. 2, will be such as to ensure tightness, which tightness is also obtainable by means of suitable seals not shown herein.

I claim:

1. A sterilizing container device for dental tools comprising: a container body consisting of a first supporting part having a head adapted to locate and support dental tools separately thereon and a second receiving part adapted to receive and support said first part in a first position wherein the latter is received within said second part and means sealingly securing said parts in said first position wherein only said head is outside said receiving part, and a second position wherein substantially all of said supporting part extends upwardly from the upper end of said receiving part; and a closure cap closing said head and being sealingly secured to said first part over said head in an airtight manner.

2. The device according to claim 1 wherein both the container body and the cap are provided with gripping embossments.

3. The device according to claim 1 wherein the container body is of right-cylindrical shape.

4. The device according to claim 3 wherein the interengageable means for securing the container body to the tool support comprises a screw thread formed at the end of the container body opposite its closed end and a first complementary thread at the bottom of the tool support and a second complementary thread near the top of the tool support, a gripping embossment integrally formed on the head of the tool support above said second complementary thread.

5. The device according to claim 4 wherein the interengageable means for tightly securing the cap to the support head comprises complementary screw threads formed on the cap and above the embossment of the head.

6. The device according to claim 5 wherein the tool support comprises a cylindrical wall depending from the head which is of circular form with the wall being arranged to extend within the container body.

7. The device according to claim 6 wherein the tool support wall comprises at least one set of openings.

8. The device according to claim 6 or claim 7 wherein the head of the tool support has a plurality of axially extending openings, each being adapted to receive and locate a dental tool.

9. The device according to claim 8 wherein the openings in the tool support head are countersunk, each comprising an upper length of larger diameter opening to the outer face of the head and a lower length of smaller diameter opening to the inner face of the head, said bores being adapted to receive dental tools so that cutting portions of such tools can protrude below the inner face within the confines of the cylindrical wall of the support while head portions can protrude above the outer face of the support head.

10. The device according to claim 8 wherein at least two of said bores for the tools are of different type or dimensions.

11. The device according to claim 6 wherein the upper face of the tool support head comprises a diametral step defining two semicircular portions, one being raised relative to the other.

12. The device according to claim 11 wherein each semicircular portion has an equal number of bores for receiving dental tools.

* * * * *